United States Patent [19]

Xiao

[11] Patent Number: 5,553,105
[45] Date of Patent: Sep. 3, 1996

[54] POLYCHANNEL MULTIPLE-TOTAL-EXTERNAL REFLECTION NEUTRON RADIOGRAPHY

[75] Inventor: Qi-Fan Xiao, Albany, N.Y.

[73] Assignee: X-Ray Optical Systems, Inc., Albany, N.Y.

[21] Appl. No.: 332,410

[22] Filed: Oct. 31, 1994

[51] Int. Cl.$^6$ .................................................. G01N 23/05
[52] U.S. Cl. ..................... 376/159; 376/110; 250/390.02
[58] Field of Search .................................... 376/159, 110; 250/390.02

[56] References Cited

U.S. PATENT DOCUMENTS

| | | | |
|---|---|---|---|
| 4,582,999 | 4/1986 | Dance et al. | 376/110 |
| 5,192,491 | 3/1993 | Schulz | 376/159 |
| 5,192,869 | 3/1993 | Kumakhov | 250/505.1 |

OTHER PUBLICATIONS

Nature, vol. 357, Jun. 1992, pp. 390–391, Kumakhov et al.
Nature, vol. 357, Jun. 1992, pp. 391–393, Chen et al.
*Neutron Radiography, Methods, Capabilities, and Applications* by Harold Berger, Elsevier Pub. Co., (1965), pp. 95–112.

*Primary Examiner*—Harvey E. Behrend
*Attorney, Agent, or Firm*—Lieberman & Nowak

[57] ABSTRACT

A method of generating a neutron-radiographic image of a sample by passing a generated neutron beam through a multiple-channel, multiple-total-external reflection neutron bender/filter manipulator which includes at least one multiple-channel element, directing an output beam from the neutron bender/filter manipulator onto the sample; passing a neutron beam exiting the sample though a multiple-channel, multiple-total-external reflection neutron scatter-rejection manipulator which includes at least one multiple-channel element, the multiple-channel element being comprised of a material containing a nuclear isotope which is highly absorptive to neutrons with energies less than approximately 10,000 eV; and detecting a beam which exits the scatter-rejection manipulator.

1 Claim, 1 Drawing Sheet

POLYCHANNEL MULTIPLE-TOTAL-EXTERNAL REFLECTION NEUTRON RADIOGRAPHY

FIELD OF THE INVENTION

The subject invention relates broadly to the detection of various substances in a sample by the scattering or the absorption of neutrons. More particularly, the invention relates to a neutron radiography device which comprises multiple-channel, multiple-total-external reflection optics. The invention also relates to an improved method of neutron radiography using multiple-channel, multiple-total-external reflection optics.

BACKGROUND OF THE INVENTION

1. Neutron Radiography

It is well known that certain nuclear isotopes, such as 1-hydrogen $^1H$, 6-lithium $^6Li$, 10-boron $^{10}B$, and others, have the property of presenting a particularly high probability of absorbing or scattering incident neutrons which have energies of roughly less than 10,000 eV. The established art of neutron radiography is a method by which such preferential absorption or scattering is exploited to enable the imaging of objects containing significant concentrations of neutron absorbing or neutron scattering nuclear isotopes. See, for example, *Neutron Radiography*, by H. Berger (Elsevier Publishing Co., New York, 1965).

In conventional neutron radiography, a sample to be analyzed is typically irradiated with an incident neutron beam. A neutron-sensitive detector is placed some distance behind the sample relative to the direction of incidence of the irradiating neutron beam to record the spatial pattern of neutron intensities exiting from the sample. Variation of neutron intensities as a function of position due to scattering or absorption in the sample can allow an image to be formed. Conventionally, the neutron-sensitive detector consists of a special photographic emulsion which is sensitive to neutrons, although other types of neutron-sensitive detectors have been used as well. Neutron radiography can also be used to determine the concentration and location of neutron absorbing or scattering materials in a sample.

Although neutron radiography has had wide application in the past to produce images of neutron absorbing or scattering bodies, it has been recognized that the quality of such images is not as great as might be desired. Among the more significant resolution-limiting factors that typically influence image quality in conventional neutron radiography are: (1) the divergence of the incident neutron beam; (2) the presence of high-energy neutrons and gamma rays in the incident beam; and (3) the interference of scattered neutrons.

The first resolution-limiting factor, neutron-beam divergence, generally has a substantial influence on the spatial resolution of the neutron radiographic image. Spatial resolution is by definition the ability to differentiate between two closely spaced objects. Because of the high intensity of the neutron beams which can be produced, nuclear reactors are the preferred neutron source for many neutron radiography applications. For the case of cold neutrons—that is, neutrons with an energy of less than about 0.01 eV—beam guides are used to direct neutrons from the reactor core to the experimental stations at which the neutron radiography is performed. The actual beam divergence at the experimental station for conventional reactor-based systems is determined by the critical angle of total external reflection for the material which is used to coat the inner surfaces of the neutron beam guides. The divergence of the beam exiting the guides is roughly twice the critical angle of the guide-coating material. Many reactor facilities use $^{58}Ni$ as a guide coating-material because it has a particularly large critical angle for neutrons in the energy range of interest, which allows efficient neutron transport. See H. J. Prask et al., *Journal of Research of the National Institute of Standards and Technology*, volume 98, page 1 and following (1993). The $^{58}Ni$ beam-guide-coating material leads to a divergence of roughly 16 mrad for neutrons with a wavelength of approximately 4 Å.

To reduce the deleterious effects which beam divergence has on spatial resolution in conventional nuclear radiography, it is usually desirable to locate the neutron sensitive detector as close as possible to the sample. However, it is not always possible to locate the detector close enough to obtain images of the spatial resolution desired. For example, in the case of determining the $^{10}B$ concentration in a brain tumor in a rat, the detector must be located outside of the head of the rat and thus spaced at least some millimeters away from the tumor. Such a distance can lead to a perceptible loss of resolution of the nuclear radiographic image of the tumor. Moreover, the closer the neutron-sensitive detector is to the sample, the more the image will be degraded by the third factor noted above; namely interference from neutrons scattered from the sample. Thus in conventional neutron radiography, there is generally a trade-off between increasing spatial resolution and decreasing noise caused by scattered neutrons.

Neutron beam collimation devices are known to the art for reducing neutron beam divergence such as various slit arrangements or Soller slits. Such neutron-beam collimation devices generally work by tending to eliminate neutrons with more than a specified amount of divergence. Unfortunately, conventional collimation devices substantially reduce the intensity of the resulting collimated beam. As a consequence of the reduced neutron intensity, longer exposure times are required, which makes the formation of clear images more difficult. A need exists in neutron radiography for a method to decrease neutron beam divergence for increased spatial resolution, while minimizing the loss of collimated-beam neutron intensity.

As for the second resolution-limiting factor noted above, neutron beams typically contain substantial concentrations of high energy neutrons and gamma rays. It is generally desirable to filter out such high energy radiation, because the attenuation of the intensities of high energy neutrons and gamma rays by a sample is usually considerably less than for the lower energy neutrons and because many neutron sensitive detectors are essentially unable to discriminate between the desired lower-energy neutrons and the higher energy radiation. The presence of high energy neutrons and gamma rays in the incident neutron beam consequently tends to lead to a decrease in image contrast. Many conventional neutron radiographic systems have an essentially line-of-sight layout; that is, the neutron source, sample, and neutron-sensitive detectors are all substantially located on a straight-line axis. Filters currently used to filter the unwanted high energy radiation generally also tend to block a portion of neutrons in the desired energy range. In conventional neutron radiography, it has proven difficult to filter out efficiently unwanted high energy radiation.

Turning now to the third factor limiting image quality in neutron radiography, neutrons of the desired energy range which are scattered from the sample also degrade the radiographic image produced by the absorption or scattering of neutrons by the sample. Locating the neutron-sensitive detector further from the sample is one method to decrease the effects of radiation scattered from the sample. However, as mentioned above, as the distance from the sample to the detector increases, there is a loss of spatial resolution in the neutron radiographic image as a result of the divergence of the incident neutron beam.

Known to the art are anti-scatter grids for reducing the effects of scattered neutrons. Anti-scatter grids are typically composed of fine meshes of neutron absorbing materials. Such anti-scatter grids function by absorbing scattered neutrons which strike the absorbing material, thus producing a more collimated beam which is less sensitive to sample-detector separation. The process is also known as scatter rejection. Unfortunately, conventional anti-scatter grids tend to block a substantial portion of the desired radiation. Moreover, such anti-scatter grids are generally expensive to manufacture. There is a need in the art for a more efficient and cost effective mechanism for improving the resolution of nuclear radiographic images.

2. Multiple-Channel, Multiple-Total-External Reflection Optics

Multiple-channel, multiple-total-external reflection optics—referred to as Kumakhov optics—are known which are based on the phenomena of total-external reflection of x rays, gamma rays, and neutrons. Multiple-channel, multiple-total-external reflection optics are described in U.S. Pat. No. 5,192,869 to Kumakhov, the contents of which are incorporated herein by reference. The critical angle of total-external reflection; that is, the angle below which incident radiation is totally reflected, is dependent on the reflecting material and on the energy of the incident radiation. In general, for a given reflection material, the lower the energy of the incident radiation, the greater the critical angle. Multiple-channel, multiple-total-external reflection optical devices include a plurality of channels. That portion of radiation which is incident on interior surfaces of the channels at angles less than the critical angle will undergo successive total reflections within the channels, and in this way can be guided along the channel interiors. The channels can be curved to manipulate radiation beams in various ways. Multiple-channel, multiple-total-external-reflection optics have demonstrated the ability to guide thermal and cold neutrons efficiently. See, for example, M. A. Kumakhov and V. A. Sharov, Nature (London), volume 357, pages 390 and following (1992) and H. Chen et al., ibid., page 391 and following.

It is an object of the present invention to decrease the divergence of a neutron beam, with a minimum loss of neutron intensity. It is another object of this invention to provide a cost-effective means to filter out high energy neutrons and gamma rays from neutron beams. Yet another object of this invention is to filter out by absorption, unwanted neutrons which are scattered from an analysis sample. Another object of this invention is to improve the quality, and sensitivity of neutron radiographic images.

SUMMARY OF THE INVENTION

The subject invention provides a neutron radiographic device which comprises multiple-channel, multiple-total-external reflection optics The subject invention further provides a neutron radiographic method of generating an image of a sample which comprises: (a) generating a neutron beam; (b) passing the neutron beam through a first multiple-channel, multiple-total-external reflection neutron manipulator, which includes at least one multiple-channel element; (c) directing an output beam from the first manipulator onto a sample; (d) passing the beam exiting the sample through a second multiple-channel, multiple-total-external reflection neutron manipulator which includes at least one multiple-channel element, which is comprised of a material containing lithium, boron, or other material which is highly absorptive to neutrons with energies less than approximately 10,000 eV; and (e) detecting the beam which exits the second manipulator.

The first multiple-channel, multiple-total-external reflection neutron manipulator is preferably formed and composed of materials effective to filter out substantially high energy neutrons and gamma rays from beams of lower energy neutrons. Such filtration may be accomplished based on the energy dependence of the critical angle. The energy dependence of the critical angle depends on the material of which reflecting surfaces of the first manipulator are composed. A preferred first multiple-channel, multiple-total-external reflection neutron manipulator of the invention includes a multichannel element which takes the form of a single bend. Such a neutron manipulator may be referred to as a neutron-bender/filter. Consider a neutron beam with a wide energy spectrum incident at a given angle on such a multiple-channel, multiple-reflection optic neutron bender. The high energy portion of the incident neutron beam, for which the incident angle is greater than the critical angle, will pass straight through the neutron bender/filter and not follow the curved path of the channels through the bend. At the same time, the lower energy portion of the incident radiation spectrum, for which the incident angle is less than the critical angle, will be captured, undergo successive reflections, and be guided along the curved path of the channels through the bend. In this way, energy filtration may be achieved. Moreover, the divergence of the neutrons exiting the neutron bender/filter can be controlled by choice of the channel material, which determines the critical angle, and the bending radius.

The second multiple-channel, multiple-total-external reflection neutron manipulator of the invention preferably includes a multiple-channel element in which the multiple channels extend essentially parallel to one another in an essentially straight-line direction. The channels are constructed with walls of materials which contain lithium, boron, or other element which is highly absorptive to neutrons with energies less than approximately 10,000 eV to provide post-sample scatter rejection. In comparison with conventional anti-scatter grids, such a preferred scatter-rejection manipulator of the invention would be expected to transmit a higher portion of the desirable unscattered neutrons, while still absorbing a substantial fraction of the unwanted scattered neutrons. In this way an improved image of the sample may be obtained with the invention.

The invention can, for example, be used to advantage in materials analysis to detect the presence and location of neutron-absorbing or neutron scattering substances or to image areas with substantial concentrations of such substances. A most advantageous application of the invention is to determine the dose of $^{10}B$ delivered to a tumor in an animal brain, to aid in the evaluation of $^{10}B$ delivery methods used in boron neutron capture therapy.

DETAILED DESCRIPTION OF BEST AND PREFERRED MODES OF CARRYING OUT THE INVENTION

Figure 1:
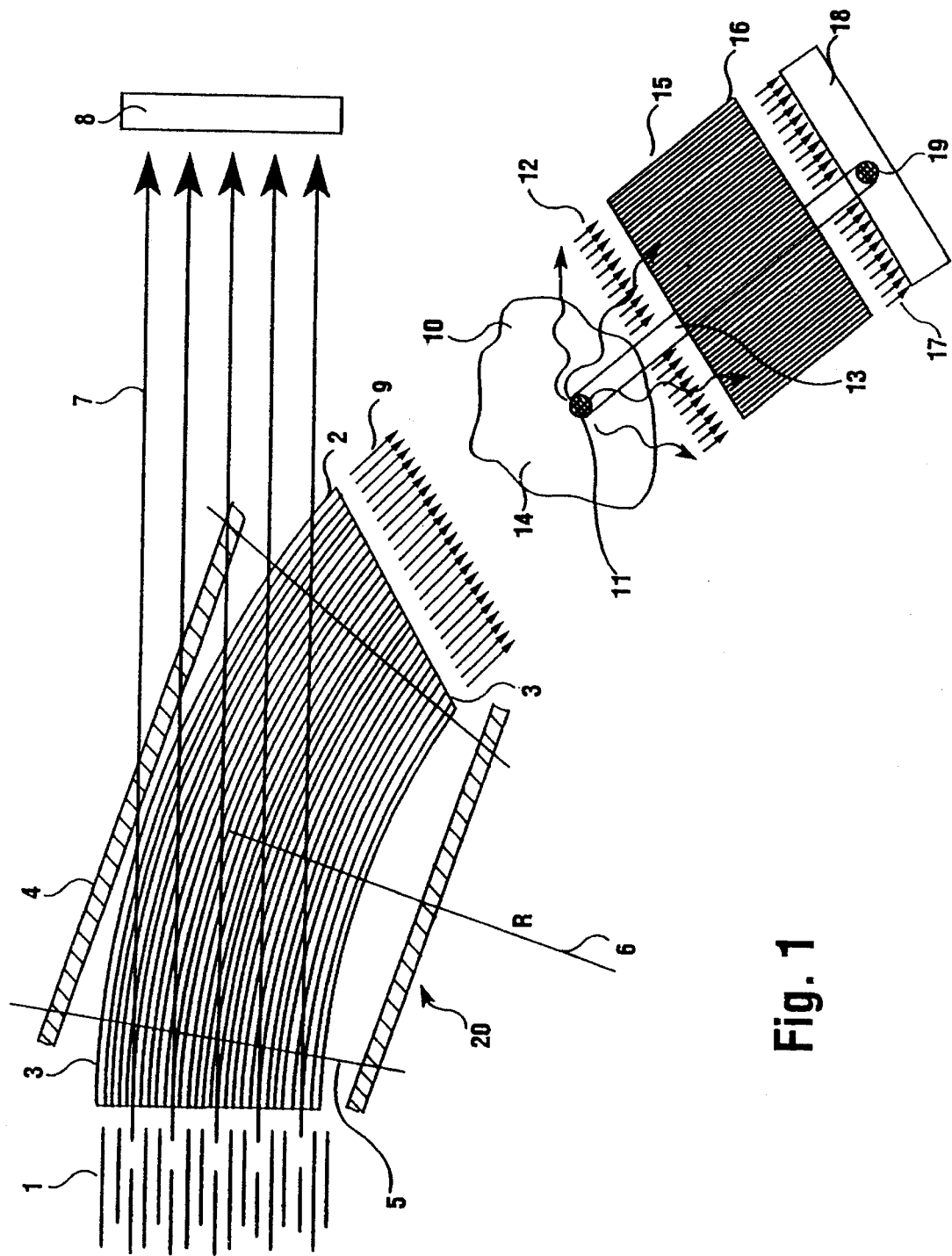
FIG. 1 is a schematic diagram of a preferred embodiment of the subject invention.

Referring now to the FIG. 1, a beam of neutrons 1 containing a wide spectrum of neutron energies and gamma radiation is incident on an input face of a first multiple-channel, multiple-total-external reflection neutron bender/filter 20, which includes at least one multiple-channel element 2. The multiple-channel element 2 has a plurality of channels 3 formed by glass capillary fibers having capillary channel passageways extending longitudinally through the fibers. Each individual capillary fiber preferably comprises a substantially unitary structure with a plurality of separate capillary channel passageways passing longitudinally through it. Preferably, the inside diameter of each of the capillary channel passageways is in the range of from about 1 to about 30 micrometers. Such capillary elements may be referred to as "polycapillaries."

The glass capillary fibers of the neutron bender/filter 20 are held substantially rigidly in the multiple-channel element 2 by a support structure 4, which includes frames 5 which hold the capillary fibers in close-packed fashion. The areal density of the channel passageways at the beam exit face of the neutron bender/ filter 20 is preferably from roughly $0.1 \times 10^6$ to roughly $50 \times 10^6$ passageways/cm$^2$. The glass capillary fibers of the neutron bender/filter 20 which are shaped to form a single, generally circular bend. The energy of the neutrons which are transmitted through the manipulator can be controlled by choosing the capillary diameter, and bending radius 6. Preferably, the bending radius is in the range of from about 1 to about 10 meters and the bending angle is preferably about 10°.

The glass of the capillaries of the neutron bender/filter 20 preferably contains a minimum of hydrogen, lithium, boron, and other elements which include isotopes highly absorptive to neutrons with energies less than approximately 10,000 eV. As a result of the preferred glass composition, the channels 3 of the neutron bender 20 tend to transmit efficiently neutrons in the most favorable energy range. The capillary fibers of the neutron bender/filter 20 are preferably comprised of a boron-free lead glass. A particularly preferred glass for the capillary fibers of the neutron bender has an approximate composition of:

45.5 weight percent $SiO_2$
29.3 weight percent PbO
15.4 weight percent $K_2O$
5.0 weight percent SrO
4.8 weight percent BaO.

The density of the preferred boron-free lead glass is about 3.26 g/cm$^3$.

The unwanted high energy neutrons and gamma rays 7 in the incident beam 1, whose critical angles for total-external reflection are significantly smaller than the critical angles for the desired low energy neutrons, strike the channel walls of the capillary passageways of the neutron bender/filter 20 at angles greater than their critical angles and pass essentially straight through the bender/filter 20 into a fast-neutron-and-gamma-ray dump 8. The neutrons of the desired lower energy 9 are guided through successive total-external reflections from the interior walls of the capillary passageways of the neutron bender/filter 20 around the bend of the bender/filter and are directed onto a sample 10.

The beam exiting the neutron bender/filter 20 is not only substantially free of high energy neurons and gamma rays, but can also have decreased divergence relative to the beam directed onto an input face of the bender/filter. For example, if the incident beam 1 is taken from a conventional $^{58}$Ni-coated beam guides from a nuclear reactor, and the multiple-channel, multiple-total-external reflection optic channels of the neutron bender 20 are formed from a preferred boron-free lead glass, then the divergence of the beam can be reduced from approximately 16 mrad to roughly 8 mrad for neutrons with a wavelength of approximately 4 Å.

The sample 10 contains a body 11 with a relatively high concentration of nuclear isotopes which are more highly absorptive to lower energy neutrons than the bulk of the sample. Most of the neutrons which impinge upon the sample 10 pass through the sample with very little attenuation 12. Those neutrons which impinge upon the absorptive body 11 are attenuated to a greater degree, leaving a "shadow" gap 13 in the neutron intensity exiting the sample. The absorptive body 11 also scatters a fraction of the neutrons incident upon it to produce scattered neutrons 14.

The neutrons exiting the sample then pass to an input face of a second neutron manipulator 15, which acts as a scatter rejection system. A preferred embodiment for the scatter-rejection manipulator 15 has channels 16 formed from glass capillary fibers, each of which ha a plurality of capillary passageways extending through it in a longitudinal direction. The inside diameters of the channel passageways of the capillary fibers of the scatter-rejection manipulator 15 are in the range of from roughly 1 to roughly 30 micrometers. The capillary fibers of the scatter-rejection manipulator 15 extend essentially parallel to one another in an essentially straight-line fashion. The areal density of capillary-channel passageways of the scatter-rejection manipulator 15 is preferably in the range of from approximately $0.1 \times 10^6$ to approximately $50 \times 10^6$ passageways/cm$^2$. The length of the capillary fibers of the scatter rejection manipulator 15 can vary over a wide range, with a length of about 20 cm being preferred. An axis of the scatter-rejection manipulator 15 defined by the direction of the capillary passageways of the manipulator extends essentially coaxially with a beam exit direction defined with respect to the neutron bender/filter 20.

Since a function of scatter-rejection manipulator 15 is to absorb scattered neutrons, the glass of the capillary fibers of the manipulator preferably includes lithium or boron isotopes which absorb neutrons. Glasses which contain boron are particularly preferred. Boron-containing borosilicate glasses with sufficiently high boron concentrations are readily available, and can be cost effective. A borosilicate glass of the following approximate composition is preferred for the capillary fibers of the scatter-rejection manipulator 15:

67 weight percent $SiO_2$
18 weight percent $B_2O_3$
9 weight percent $K_2O$
3 weight percent $Al_2O_3$
2 weight percent Li
1 weight percent $Na_2O$.

The density of the preferred borosilicate glass is about 2.29 g/cm$^3$.

The walls of preferred capillary fibers form the support structure, so that the whole scatter-rejection manipulator 15 is a substantially unitary structure. A manipulator of this form may be called monolithic.

A substantially collimated neutron beam 17 which exits the scatter-rejection manipulator 15 is directed onto a neutron-sensitive detector 18, which forms a "shadow" image 19 of the absorbing body 11 in the sample 10. The detector is preferably a photographic emulsion which is sensitive to neutrons coated on a photographic plate. Other neutron-sensitive detectors could be used if desired.

In another preferred embodiment, the sample can be rotated or otherwise reoriented in a predetermined way and a series of neutron radiographs taken for a sequence of sample orientations. The series of neutron radiographs could then be used to construct a three-dimensional image of neutron-absorbing portions of the sample.

Upon reading the above specification, variations and alternative embodiments will become obvious to one skilled in the art, and are considered within the scope and spirit of the subject invention.

What is claimed is:

1. A method of generating a neutron-radiographic image of a sample which comprises:

(a) generating a neutron beam;

(b) passing the neutron beam through a multiple-channel, multiple-total-external reflection neutron bender/filter manipulator, which includes at least one multiple-channel element;

(c) directing an output beam from the neutron bender/filter manipulator onto the sample;

(d) passing a neutron beam exiting the sample through a multiple-channel, multiple-total-external reflection neutron scatter-rejection manipulator which includes at least one multiple-channel element, the multiple-channel element being comprised of a material containing a nuclear isotope which is highly absorptive to neutrons with energies less than approximately 10,000 eV; and (e) detecting a beam which exits the scatter-rejection manipulator.

* * * * *